(12) United States Patent
Lai

(10) Patent No.: US 11,819,240 B2
(45) Date of Patent: Nov. 21, 2023

(54) ANCILLARY SYSTEM HAVING AN EXHAUST DEVICE FOR SURGERY

(71) Applicant: National Taiwan University Hospital, Taipei (TW)

(72) Inventor: Shuo-Lun Lai, Taipei (TW)

(73) Assignee: National Taiwan University Hospital

( * ) Notice: Subject to any disclaimer, the term of this patent is extended or adjusted under 35 U.S.C. 154(b) by 210 days.

(21) Appl. No.: 16/631,095

(22) PCT Filed: Jul. 20, 2018

(86) PCT No.: PCT/US2018/043021
§ 371 (c)(1),
(2) Date: Jan. 14, 2020

(87) PCT Pub. No.: WO2019/018726
PCT Pub. Date: Jan. 24, 2019

(65) Prior Publication Data
US 2020/0229839 A1 Jul. 23, 2020

(30) Foreign Application Priority Data
Jul. 21, 2017 (TW) .................................. 106124515

(51) Int. Cl.
*A61B 17/3211* (2006.01)
*A61B 17/34* (2006.01)
(Continued)

(52) U.S. Cl.
CPC ...... *A61B 17/3211* (2013.01); *A61B 17/3421* (2013.01); *A61B 17/320068* (2013.01);
(Continued)

(58) Field of Classification Search
CPC .. A61B 17/3211–2017/32113; A61B 17/3213; A61B 17/3421; A61B 17/3417;
(Continued)

(56) References Cited

U.S. PATENT DOCUMENTS 4,451,257 A * 5/1984 Atchley ............... A61M 1/7413
604/119
4,589,414 A 5/1986 Yoshida et al.
(Continued)

FOREIGN PATENT DOCUMENTS

CN 203280484 U 11/2013
CN 203873875 10/2014
(Continued)

OTHER PUBLICATIONS

Translation of Abstract for TW I552715.
(Continued)

*Primary Examiner* — Robert A Lynch
*Assistant Examiner* — Brigid K Byrd
(74) *Attorney, Agent, or Firm* — BEHMKE INNOVATION GROUP LLC; James M. Behmke; Keith O. Mitchell

(57) ABSTRACT

An ancillary system for surgery is provided. The ancillary system includes a trocar, a scalpel device and an exhaust device. The scalpel device includes a blade portion and a connecting arm. The exhaust device encapsulates at least a portion of the connecting arm of the scalpel device. The exhaust device is detachable from the scalpel device, and is configured to remove smoke, body fluids or biological tissues generated during a surgery to effectively improve the surgical process.

13 Claims, 10 Drawing Sheets

(51) Int. Cl.
*A61B 17/32* (2006.01)
*A61B 18/20* (2006.01)
*A61B 17/00* (2006.01)
*A61B 18/12* (2006.01)

(52) U.S. Cl.
CPC ... *A61B 18/201* (2013.01); *A61B 2017/00902* (2013.01); *A61B 2017/32113* (2013.01); *A61B 2018/126* (2013.01); *A61B 2217/005* (2013.01); *A61B 2217/007* (2013.01); *A61B 2218/008* (2013.01)

(58) Field of Classification Search
CPC ...... A61B 2017/3437; A61B 2218/008; A61B 2018/1412; A61B 2018/146; A61B 18/1482; A61B 18/1487; A61B 2017/32007; A61B 2017/00902; A61B 2217/005; A61M 1/76; A61M 1/0023; A61M 39/223–2039/224
See application file for complete search history.

(56) References Cited

U.S. PATENT DOCUMENTS

| | | | | |
|---|---|---|---|---|
| 4,919,129 | A * | 4/1990 | Weber, Jr. | A61B 18/1402 606/42 |
| 5,314,406 | A * | 5/1994 | Arias | A61M 5/1418 604/21 |
| 5,348,555 | A * | 9/1994 | Zinnanti | A61B 18/1482 606/49 |
| 5,391,144 | A * | 2/1995 | Sakurai | A61B 17/22012 604/22 |
| 5,449,357 | A * | 9/1995 | Zinnanti | A61M 1/0062 606/49 |
| 5,527,276 | A * | 6/1996 | Bruce | A61B 17/3415 604/506 |
| 5,551,448 | A * | 9/1996 | Matula | A61B 50/30 128/897 |
| 5,662,647 | A | 9/1997 | Crow et al. | |
| 5,830,214 | A | 11/1998 | Flom et al. | |
| 6,142,995 | A | 11/2000 | Cosmescu | |
| 6,592,543 | B1 | 7/2003 | Wortrich et al. | |
| 7,955,318 | B1 * | 6/2011 | Schultz | A61M 1/84 604/319 |
| 2003/0009130 | A1 * | 1/2003 | Stecker | A61M 1/85 604/104 |
| 2003/0050603 | A1 * | 3/2003 | Todd | A61B 17/3421 604/164.02 |
| 2009/0270818 | A1 | 10/2009 | Duke | |
| 2014/0336634 | A1 | 11/2014 | Gomez | |
| 2016/0106952 | A1 | 4/2016 | Mastri et al. | |

FOREIGN PATENT DOCUMENTS

| | | |
|---|---|---|
| CN | 203873875 U | 10/2014 |
| CN | 204562392 U | 8/2015 |
| DE | 4415360 A1 | 11/1995 |
| DE | 202010015327 | 1/2011 |
| EP | 2946738 | 11/2015 |
| IN | 2017/21000186 | 3/2017 |
| TW | I572313 B | 11/2014 |
| TW | 1552715 | 10/2015 |
| TW | M516423 | 2/2016 |
| TW | I579837 B | 3/2016 |
| TW | I552715 | 10/2016 |
| WO | WO-2017/061228 A1 | 4/2017 |
| WO | 2018/039239 | 3/2018 |

OTHER PUBLICATIONS

Chinese Office Action dated Feb. 3, 2020 in connection with Chinese application CN201810811412.1.
Taiwan Office Action dated Jul. 15, 2020 in connection with Taiwan application 108145516.
European Search Report for Application No. 18835470.8-1113/ 3654861 PCT/US2018043021 dated Jun. 18, 2021.
Translation of Abstract for CN 203873875.
Translation of Abstract for DE 202010015327.
Translation of Abstract for TW M516423.
Translation of Abstract for TW I572313 B.
Translation of Abstract for TW I579837 B.

* cited by examiner

ANCILLARY SYSTEM HAVING AN EXHAUST DEVICE FOR SURGERY

BACKGROUND

1. Technical Field

The present disclosure relates to an ancillary system for surgery, and more particularly, to an ancillary system having an exhaust device for surgery.

2. Description of Related Art

Since the 1990s, laparoscopic surgery has flourished for more than 20 years, and relevant technologies and devices are changing with each passing day. Laparoscopic surgery is typically performed in an anesthetized human body by using a camera with a high-sensitivity resolution, a scalpel device, and various precision instruments simultaneously through a trocar having a protective sleeve and a tubular passage.

Conventionally, bleeding issues caused in laparoscopic surgery can be improved through electrosurgical procedures. When a laparoscopic scalpel is performed in an electrosurgical procedure, the standard principle is to use a high-frequency current generator to supply a current to the tip of a blade and transmit high-energy power to a human tissue. The power generated by the current will cause body fluids to vibrate and rub, thereby producing high-level thermal energy, which will evaporate the water among the body tissues and cause the tissues to separate or solidify. Therefore, it not merely shortens the surgical time, facilitates tissue cutting, improves wound healing, and avoids patient blood loss that leads to reduce patient safety potentially, but also reduces the possibility of infection and other complications and improves the quality in medical application.

However, one of the problems encountered in the traditional laparoscopic surgery is that high-level energy is emitted from the scalpel to the human tissues in a short time, and a large amount of smoke will be produced inside the human body chamber where it is located. The smoke plumes will easily diffuse and cause in the impairment of visual acuity.

In view of the foregoing, it is necessary to provide a novel ancillary medical system to overcome the drawbacks faced by existing prior art.

SUMMARY

Other aspects of the present disclosure will be set forth in the description which follows, and in part will be obvious to one of ordinary skill in the art after perusing the following content. One of ordinary skill in the art may also conceive the content thereof from the implementation of the present disclosure. The advantages disclosed herein may be realized and obtained as particularly pointed out in the appended claims.

In one embodiment, the present disclosure provides an ancillary system for surgery, comprising: a trocar; a scalpel device comprising a blade portion and a connecting arm connected to the blade portion; and an exhaust device disposed in the trocar and encapsulating at least a portion of the connecting arm of the scalpel device, wherein the exhaust device and the scalpel device are detachable from each other, and the exhaust device is configured for removing substance (e.g., smoke, body fluid or biological tissue) generated in a surgical process to ensure the clear view of the surgical site and the cleanliness inside the body cavity.

In one embodiment, the exhaust device of the present disclosure may be applied to a variety of scalpel devices. For example, the exhaust device may comprise a tubular structure with a head portion, and the head portion may be in a cone-shape structure comprising one or more vents arranged on a surface of the cone-shape structure. In another embodiment, in addition to the head portion, the tubular structure may have one or more additional vents formed on a sidewall of the tubular structure.

In one embodiment, at least one of the head portion and the tubular structure may be made of a transparent material (e.g., polyethylene (PE), polypropylene (PP), PE/PP copolymer, polycarbonate (PC), polytetrafluoroethylene (PTFE), polyvinylidene fluoride (PVDF), ethylene vinyl acetate (EVA), polyethersulfone (PES), polyurethane, polyethylene terephthalate (PET), glass, etc.).

In one embodiment, the exhaust device of the present disclosure may further comprise an exhaust valve module connected to the tubular structure of the exhaust device. The substance (e.g., smoke, body fluid or biological tissue) produced in a surgical process may enter the tubular structure via the vents and be discharged through the exhaust valve module.

DETAILED DESCRIPTION OF EMBODIMENTS

Figure 1A:
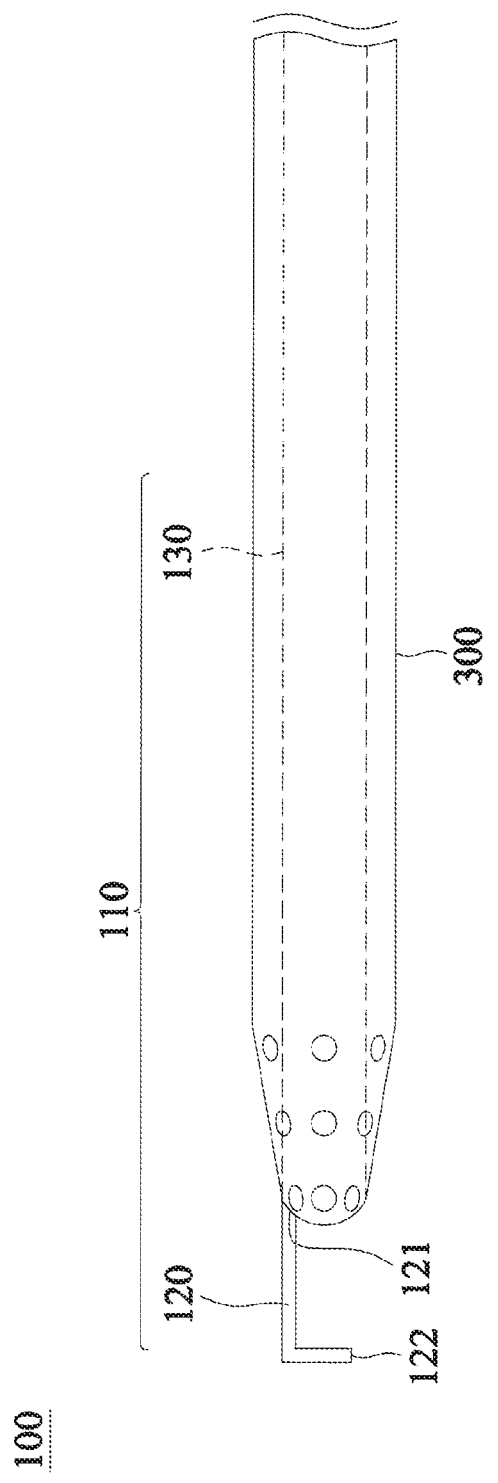
FIG. 1A is a schematic diagram of an ancillary system for surgery according to an embodiment of the present disclosure.

The following examples can make the present disclosure more comprehensively understood by one of ordinary skill in the art, but are not intended to limit the present disclosure in any way. The aspects of the present disclosure and the details thereof are explained more fully below with reference to the non-limiting examples illustrated in the accompanying drawings. Descriptions on known materials, manufacturing tools, process technologies, etc. are omitted, in order not to unnecessarily obscure the details of the present disclosure. However, it should be understood that the detailed description and specific examples, which are given to illustrate the aspects of the present disclosure, are by way of illustration and not limitation. One of ordinary skill in the art will recognize from the present disclosure that various substitutions, alterations, additions and/or arrangements may be made to the spirit and/or scope of the underlying inventive concept.

The approximate language used in the specification of the present disclosure can be used to alter any quantitative expression, which can be varied within an allowable range without causing a change in the basic function associated therewith. Thus, the value altered by one or more terms such as "about" is not limited to the precise value specified. In some examples, the approximate language may correspond to the accuracy of the instrument used to measure the value. The terminology used herein is for the purpose of describing particular examples only, and is not intended to limit the present disclosure. As used herein, the singular forms "a," "an" and "the" are intended to include the plural forms as well, unless the context clearly indicates otherwise. It should also be understood that the terms "comprise" (and any form of comprising), "having" (and any form of having), and "include" (and any form of including) are open-ended conjunction verbs. Thus, a method or device "comprising," "having" or "including" one or more steps or elements is not limited to have only those one or more steps or elements. Similarly, the steps of a method or the elements of a device that "comprise," "have" or "include" one or more features are not limited to have only those one or more features. Moreover, devices or structures configured in a particular manner are configured in at least that manner, but may also be configured in ways that are not listed.

When the term "connected" is used in the present disclosure for two physical elements, it refers to a direct connection between the two physical elements. In addition, when the term "coupled" is used for two physical elements, it may mean that the two physical elements are directly connected or connected through one or more intermediate elements. As used herein, the terms "may" and "may be" indicate a likelihood of occurrence under a series of conditions, have a particular attribution, property or function, and/or modify another verb, which occurs by expressing one or more capabilities, functions, or possibilities associated with the modified verb. Thus, considering that, in some cases, modified terms may sometimes be inappropriate, incapable, or unsuitable, the use of "may" and "may be" indicates that the modified term is clearly appropriate, capable, or suitable for the performance, function or purpose shown. For example, in some cases, an event or performance may be expected, while in other cases, the event or performance may not occur. This distinction is an embodiment of the terms "may" and "may be."

Referring now to the drawings of the present disclosure, for facilitating understanding, the drawings are not drawn to scale, wherein like reference numerals have been used throughout different drawings to designate the same or similar elements.

Figure 1B:
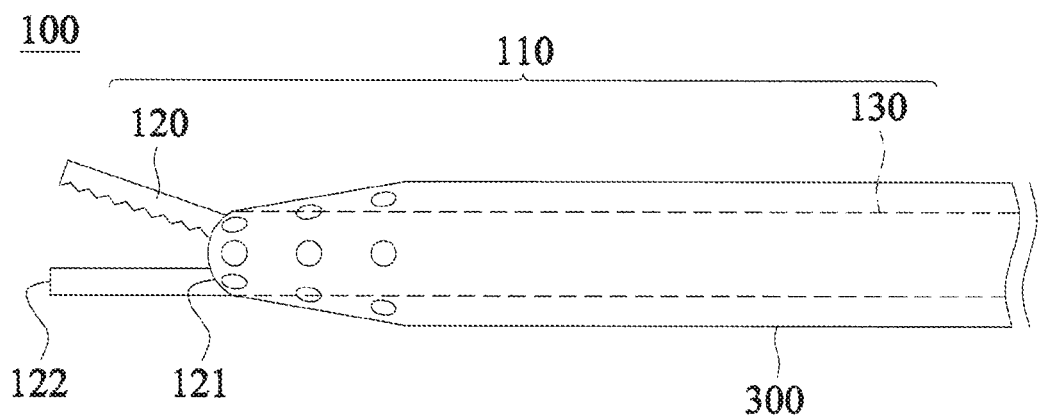
FIG. 1B is a schematic view of another ancillary system for surgery according to an embodiment of the present disclosure.
Figure 1C:
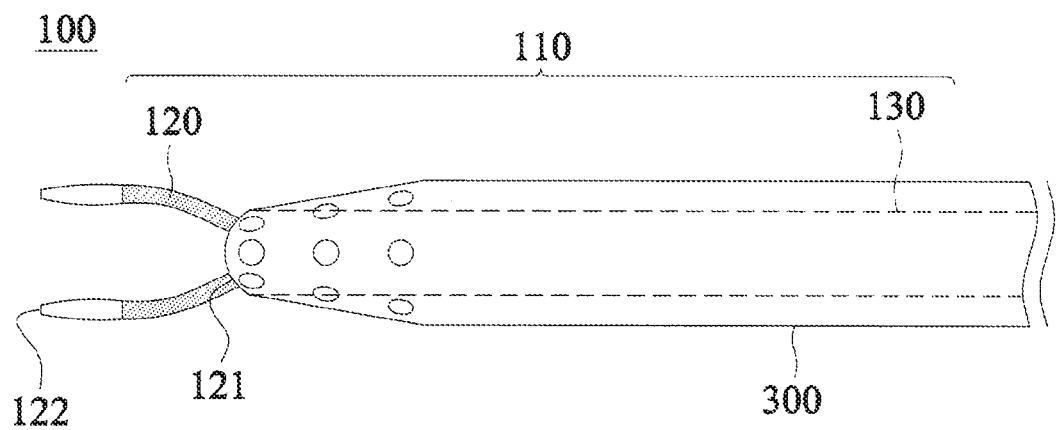
FIG. 1C is a schematic diagram of a yet another ancillary system for surgery according to an embodiment of the present disclosure.
Figure 1D:
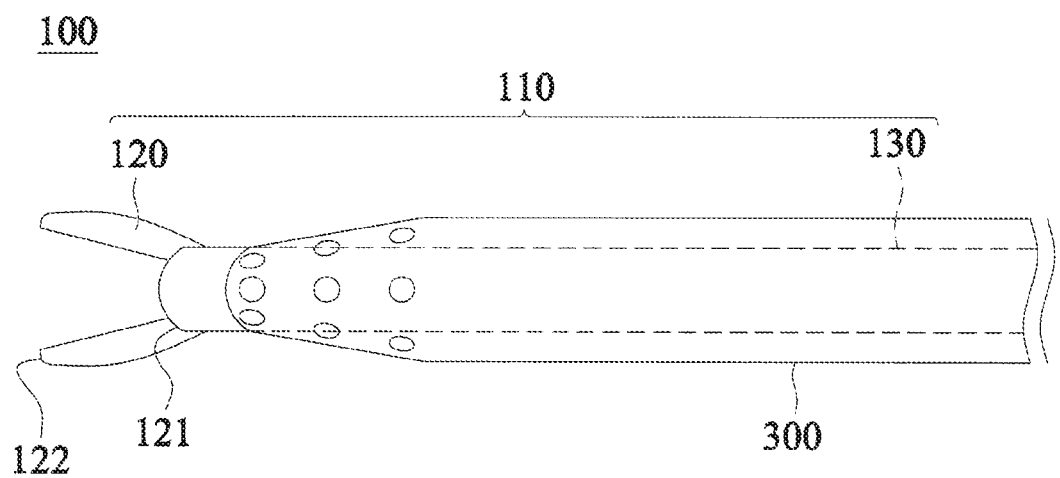
FIG. 1D is a schematic diagram of a yet another ancillary system for surgery according to an embodiment of the present disclosure.

FIG. 1A is a schematic view of an ancillary system 100 for surgery according to an embodiment of the present disclosure. As shown in FIG. 1A, the ancillary system 100 includes at least a scalpel device 110 and an exhaust device 300, wherein the scalpel device 110 includes a blade portion 120 and a connecting arm 130. The type or kind of the scalpel device 110 is not particularly limited in the present disclosure. For example, the scalpel device 110 may be an electrosurgical unit having a specific shape and function. In other embodiments, the scalpel device 110 may also be replaced with a harmonic scalpel (referring to FIG. 1B), a bipolar scalpel (referring to FIG. 1C), laser (not shown) or a tissue agglutination apparatus (Ligasure) (referring to FIG. 1D) and does not affect the effect of the present disclosure, wherein the harmonic scalpel is also called as an ultrasonic scalpel, which utilizes a metal scalpel head to oscillate and rub tissues at an ultrasonic frequency in order to separate a biological tissue or keep the biological tissue from bleeding.

Returning to FIG. 1A, the blade portion 120 is coupled to the connecting arm 130, and is controlled by the connecting arm 130. The exhaust device 300 is used to encapsulate at least a portion of, a majority of, or the entire connecting arm 130 of the scalpel device 110. In one embodiment, the exhaust device 300 is adjacent to or aligned with the bottom 121 of the blade portion 120. The exhaust device 300 is used to exhaust smoke, body fluids, or biological tissues that may be generated in the process of surgery, so as to ensure a clear surgical view and facilitate the surgery. It should be noted that the exhaust device 300 and the scalpel device 110 are separable from each other, and the exhaust device 300 and the scalpel device 110 are not integrally formed in physical design. Accordingly, when the surgery is performed, the exhaust device 300 can be sheathed on the outside of the scalpel device 110, and when the surgery is finished, the exhaust device 300 can be disassembled from the scalpel device 110 and discarded. Under such design, the exhaust device 300 can be compatible with surgical instruments of different brands, model numbers, and uses (referring to, e.g., FIGS. 1B, 1C and 1D), and can be easily disassembled from the surgical instruments to improve the surgical efficiency.

Figure 2A:
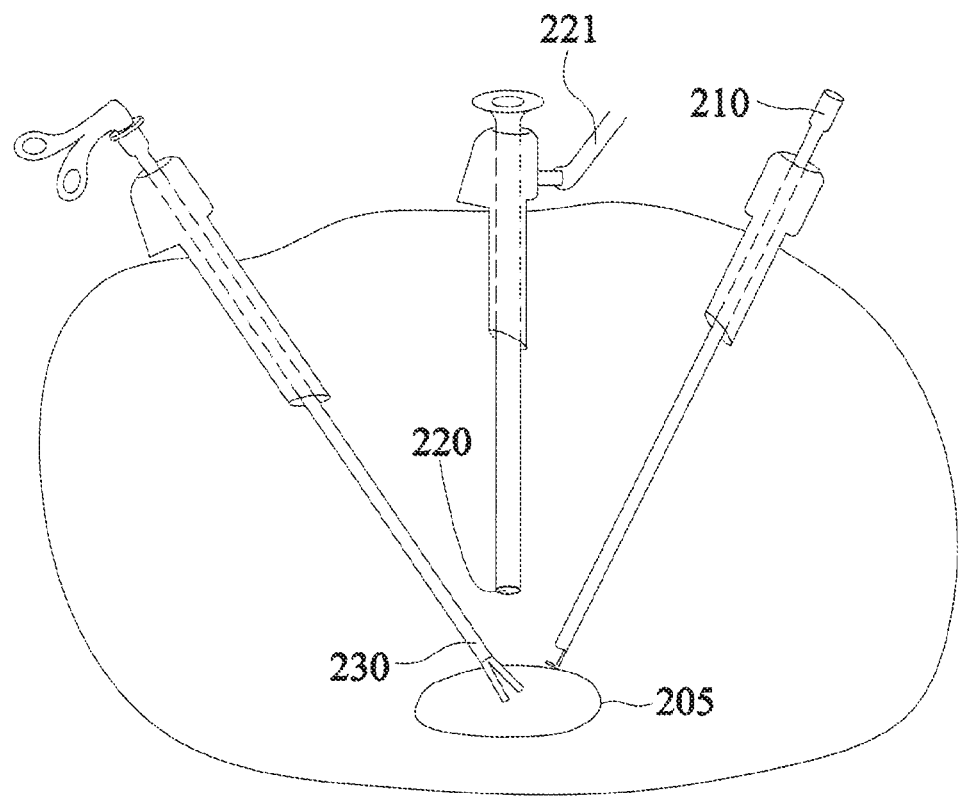
FIG. 2A is a schematic diagram of a device for traditional laparoscopic surgery.

FIG. 2A is a schematic diagram of conventional laparoscopic surgery. As shown in FIG. 2A, in conventional laparoscopic surgery, medical personnel staffing generally uses a scalpel device 210 (without any additional exhaust device), a camera lens 220 (with a carbon dioxide inlet 221), and a clamp 230. However, when the scalpel device 210 is used in an electrosurgical process on a lesion 205 (e.g., a tumor, an inflammatory tissue, or a bleeding site), it usually emits high-level energy to cells or organ tissues instantaneously, and thus a large amount of smoke will be generated. Therefore, it will cause the surgeon's visual impairment, and even cause the camera lens 220 to become fogging or soiling, which renders interruption of the surgery. As such, the interference will lengthen the procedure time, increase a surgical risk and treatment costs, and significantly decrease surgical efficiency.

Figure 2B:
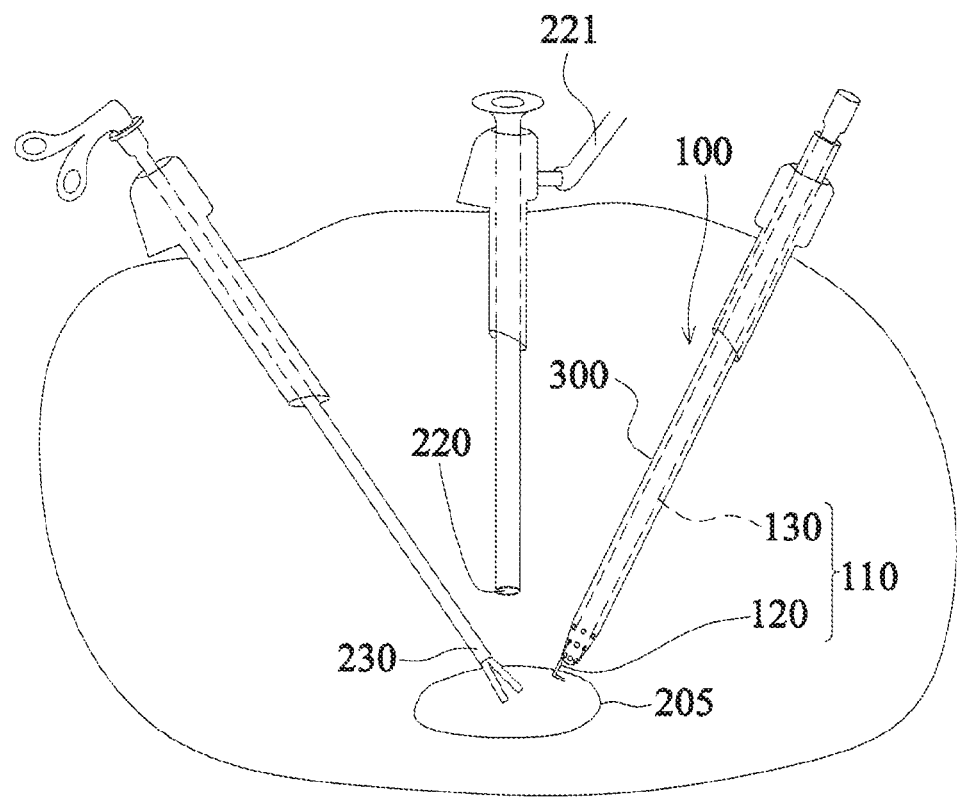
FIG. 2B is a schematic diagram of an ancillary system for surgery according to an embodiment of the present disclosure used for laparoscopic surgery.

FIG. 2B is a schematic diagram of laparoscopic surgery using an exhaust device 300 of the present disclosure. Using the scalpel device 110 (with the exhaust device 300 attached thereto) of the present disclosure to perform laparoscopic surgery will significantly improve the predicament faced by existing prior art. For example, when the scalpel device 110 is used in an electrosurgical treatment on the lesion 205, the smoke generated in the process of a surgical procedure can be simultaneously removed by sheathing the outer side of the connecting arm 130 of the scalpel device 110 with the exhaust device 300. It should be noted that since the exhaust device 300 is adjacent to the blade portion 120 of the scalpel device 110, the smoke generated by the electrosurgical process can be quickly discharged before it spreads throughout the abdominal cavity. With this type of design, the surgical time and smoothness can be effectively improved.

The following embodiments will describe more details of the exhaust device 300. It should be understood that these drawings and descriptions are merely for exemplification, and are not intended to limit the scope of the present disclosure.

Figure 3A:
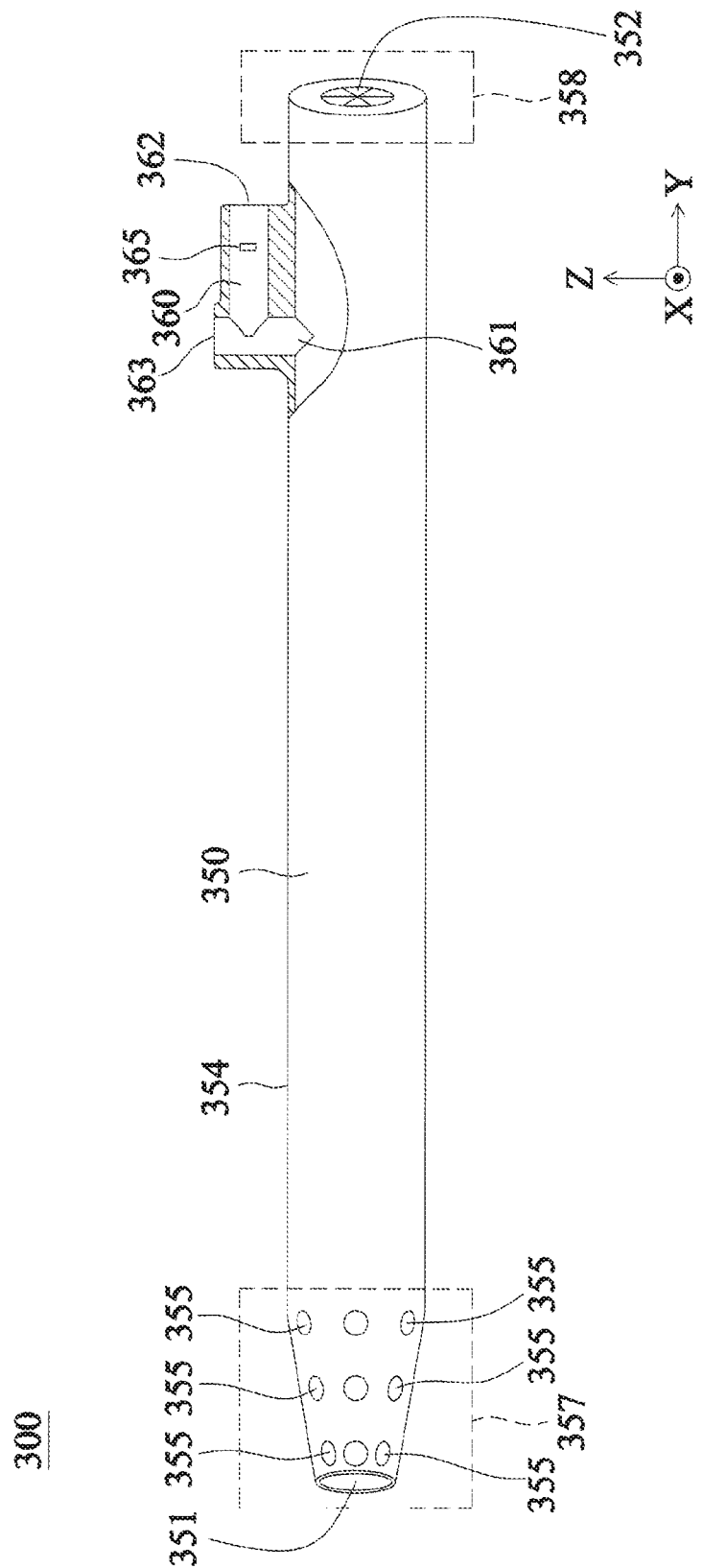
FIG. 3A is a schematic diagram of an exhaust device according to an embodiment of the present disclosure.
Figure 3B:
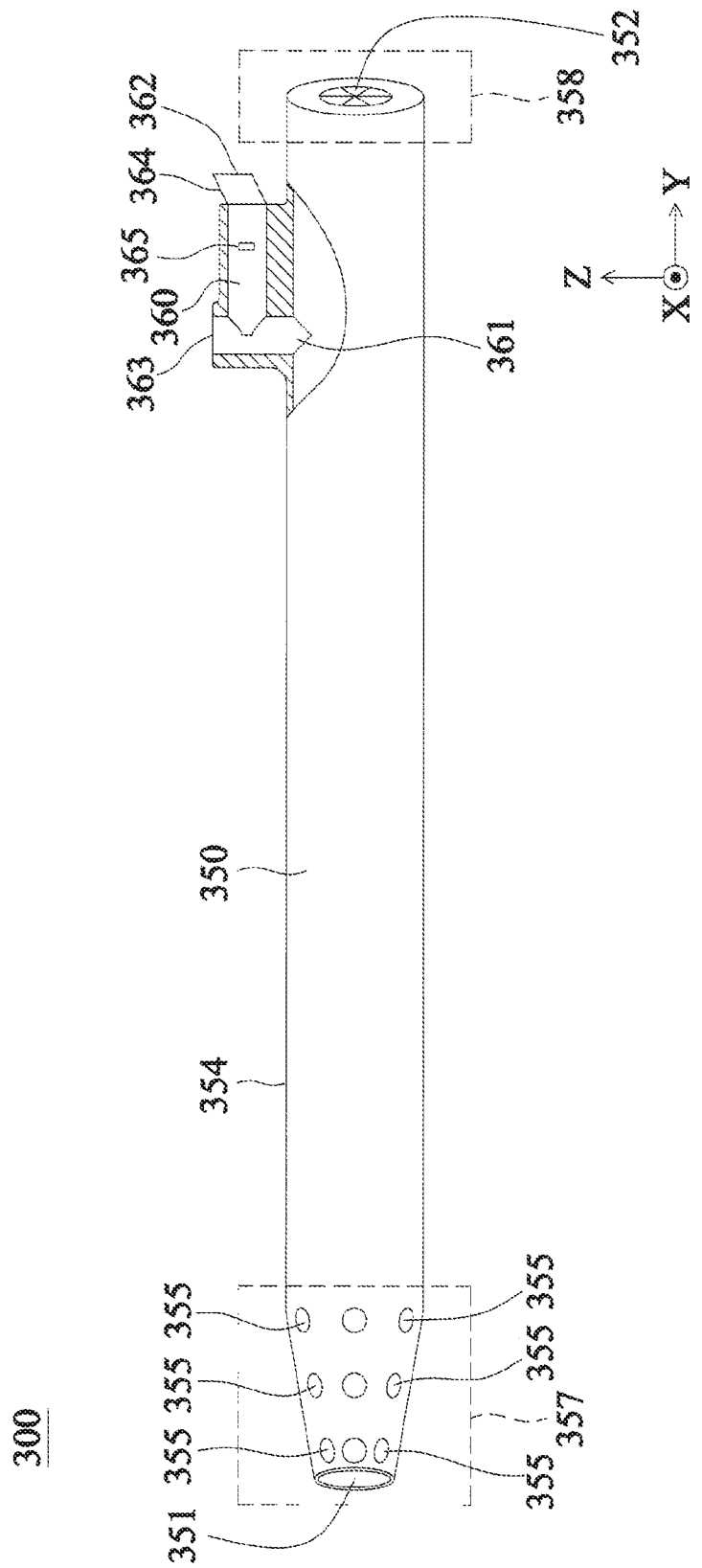
FIG. 3B is a schematic diagram of an exhaust device according to another embodiment of the present disclosure.

FIGS. 3A and 3B are schematic diagrams of the exhaust device 300 according to an embodiment of the present disclosure. In the embodiments shown in FIGS. 3A and 3B, the exhaust device 300 includes a tubular structure 350 and an exhaust valve module 360. The tubular structure 350 has a first end 351 and a second end 352; both of which are of open ends. The inner diameter of the tubular structure 350 must be larger than the maximum outer diameter of the outer wall surface of the connecting arm 130 of the scalpel device 110, so as to facilitate mutual fitting of the two. When the exhaust device 300 is sheathed on the scalpel device 110, the connecting arm 130 of the scalpel device 110 can be placed in the hollow interior of the tubular structure 350, and pass through the first end 351 and the second end 352 of the tubular structure 350. In one embodiment, the tubular structure 350 has one or more vents 355. In other embodiments, one or more vents 355 merely located on the surface of a head portion 357 of the tubular structure 350, which may be formed as a cone-shaped structure. In another embodiment, the longitudinal axis of the cone-shape structure is shifted from a central axis of the tubular structure 350.

In some embodiments, the tubular structure 350 is a hollow cylinder, and the vents 355 are all formed on a sidewall surface 354 of the hollow cylinder, and can be in communication with the interior of the tubular structure 350. For example, the vents 355 can be equidistantly or randomly distributed on the sidewall surface 354 of the tubular structure 350. The exhaust valve module 360 is connected to the tubular structure 350, wherein the substance (e.g., smoke, body fluid or biological tissue) generated in the process of a surgical procedure can enter the hollow interior of the tubular structure 350 through the vents 355 (i.e., the gap between the inner wall of the tubular structure 350 and the connecting arm 130 of the scalpel device 110), and be discharged through the exhaust valve module 360. For example, the vents 355 are arranged at the head portion 357 adjacent to the first end 351 of the tubular structure 350, and the exhaust valve module 360 is adjacent to the second end 352 of the tubular structure 350. In some embodiments, the head portion 357 of the tubular structure 350 may be a cone-shaped structure to provide better stability of the scalpel device 110. When the scalpel device 110 is sheathed by the exhaust device 300, the first end 351 of the tubular structure 350 may be adjacent to or aligned with the bottom 121 of the blade portion 120 (not shown), so that the distance between the vents 355 and the tip 122 of the blade section 120 is within about 1 to 2 cm to facilitate the elimination of smoke plumes generated in the surgery.

In some embodiments, the tubular structure 350 is a hollow cylindrical structure or one of a variety of tubular cylindrical (e.g., not pure cylindrical) structures. Based on physics mechanism of the present disclosure, the present disclosure can discharge the substance (e.g., smoke, body fluid or biological tissue) generated during a surgical process according to pressure difference via the vents 355 and the space between the tubular structure 350 and the blade portion 120 as well as the connecting arm 130. As such, no mechanical devices or transducers (e.g., motors, fans, etc.) are required to produce the driving force, nor filters to filtrate the substance (e.g., smoke, body fluid or biological tissue) in a surgical process. Accordingly, the efficiency for the substance generated during a surgical process to pass through the tubular structure 350 can be significantly improved.

In some embodiments, the tubular structure 350 is a hollow cylindrical structure or one of a variety of tubular cylindrical (not pure cylindrical) structures, and its material may be a plastic material (e.g., polyethylene (PE), polypropylene (PP), PE/PP co-polymer, polycarbonate (PC), polytetrafluoroethylene (PTFE), polyvinylidene fluoride (PVDF), ethylene vinyl acetate (EVA), polyethersulfone (PES), polyurethane, polyethylene terephthalate (PET), etc.) or a transparent material. In some embodiments, the head portion 357 of the tubular structure 350 is a transparent material, which ensures a visible field of view in the process of the surgical procedure.

In some embodiments, the exhaust device 300 can be compatible with surgical instruments of different brands, model numbers, and uses (referring to, e.g., FIGS. 1B, 1C and 1D), and can be easily removed.

In some embodiments, the head portion 357 at the first end 351 of the tubular structure 350 is also an inwardly contracted open portion, which may enable the tubular structure 350 to be gradually attached to the connecting arm 130 of the scalpel device 110. For example, the inwardly contracted open portion of the tubular structure 350 may be implemented with a conduct with unequal widths or a similar conical conduit with a tapered opening (tapering from, e.g., right to left in FIGS. 3A and 3B).

In other embodiments, the tubular structure 350 further includes a containment shield 358 located at the second end 352 of the tubular structure 350, and may enable the second end 352 (the second open end) of the tubular structure 350 to be tightly engaged with the connecting arm 130 of the scalpel device 110. For example, the containment shield 358 of the tubular structure 350 may be implemented with an element having a resilient gasket. In another embodiment, the containment shield 358 (not shown) of the tubular structure 350 may be disassembled from the tubular structure 350. When the connecting arm 130 of the scalpel device 110 passes through the second end 352 of the tubular structure 350, the containment shield 358 can be adherent to the outer wall of the connecting arm 130 to prevent gas from leaking from the second end 352 of the tubular structure 350.

In other embodiments, different from a cylindrical shape, the tubular structure 350 can be altered into different shapes based on different requirements, for example, a hollow triangular prism, a hollow quadrangular prism, or a hollow polygonal prism (not shown).

In addition, the number and arrangement of the vents 355 of the tubular structure 350 can also be modified based on different requirements. For example, fewer (at least one) or more vents 355 can be designed on the sidewall 354 of the tubular structure 350. In one embodiment, the vents 355 are all distributed adjacent to the first end 351 of the tubular structure 350. In other embodiments, one or more vents 355 may also be designed on other portions of the sidewall 354 to ensure clearness of the visible field view under the camera lens 220.

As shown in FIG. 3A, a T-shaped flow channel is arranged in the interior of the exhaust valve module 360 to provide a path in direction to removing substance (e.g., smoke, body fluid or biological tissue) generated in a surgical process. The exhaust valve module 360 has a T-shaped flow channel having a first opening 361, a second opening 362, and a third opening 363, wherein the first opening 361 may be bundled to the tubular structure 350 to communicate with the hollow interior of the tubular structure 350. For example, the first opening 361 of the T-shaped flow channel of the exhaust valve module 360 may be in the −Z axis direction; the second opening 362 of the T-shaped flow channel of the exhaust valve module 360 may be in the +Y axis direction; and the third opening 363 of the T-shaped flow channel of the exhaust valve module 360 may be in the +Z axis direction. In other embodiments, the directions of the openings of the exhaust valve module 360 can also be modified, based on practical needs. For example, as shown in FIG. 3B, the exhaust valve module 360 may further include an angled turning portion 364 to adjust the direction of the second opening 362 of the T-shaped flow channel of the exhaust valve module 360. Similarly, another angled turning portion (not shown) may also be applied to the third opening 363 to adjust the direction of the third opening 363.

In some embodiments, the exhaust valve module 360 further includes an evacuation controlling valve 365 disposed between the first opening 361 and the second opening 362 of the T-shaped flow channel of the exhaust valve module 360. By using the evacuation controlling valve 365, the first opening 361 and the second opening 362 are selectively in communication with or not in communication with each other in the exhaust valve module 360. For example, the evacuation controlling valve 365 may be a slidable plate that can be pushed into the exhaust valve module 360 or extracted from the exhaust valve module 360.

Figure 4A:
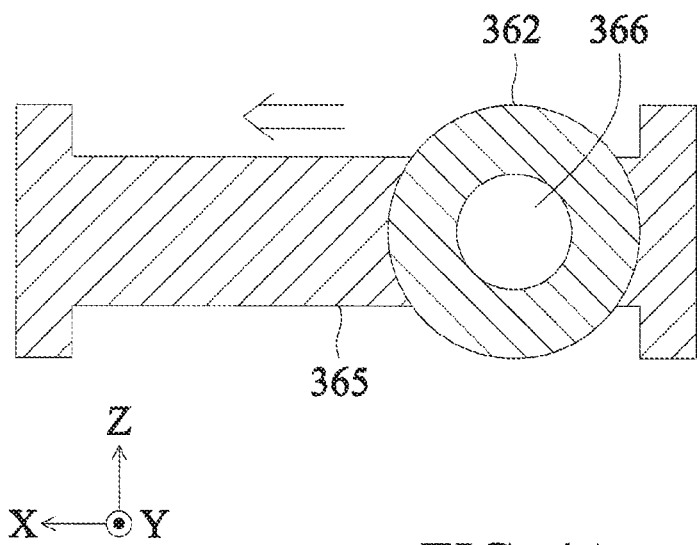
FIG. 4A is a schematic diagram of an opened air-evacuation controlling valve according to an embodiment of the present disclosure.
Figure 4B:
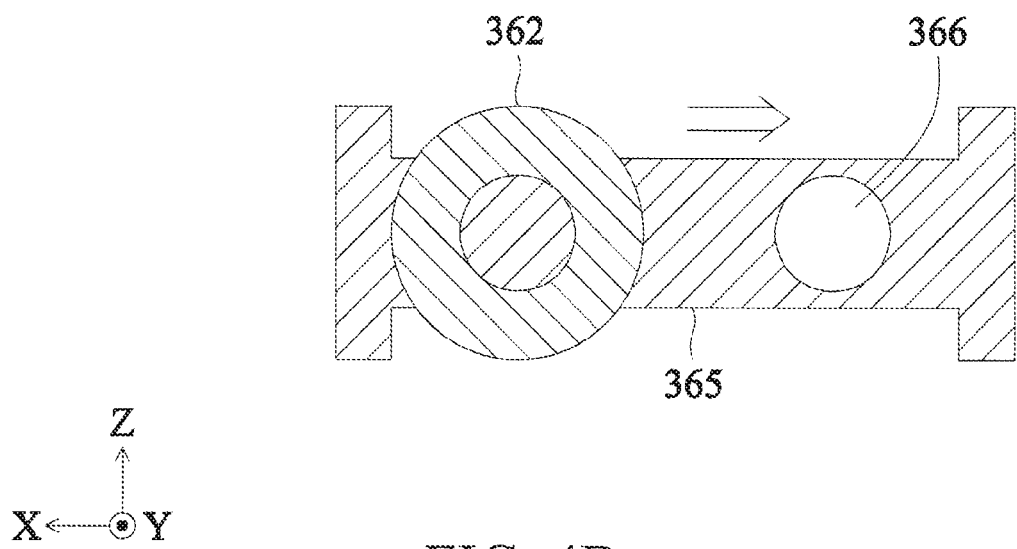
FIG. 4B is a schematic diagram of a closed air-evacuation controlling valve according to an embodiment of the present disclosure.

As shown in FIGS. 4A and 4B, the evacuation controlling valve 365 may have a through-hole 366. More specifically, FIG. 4A is a schematic diagram illustrating the opening of the evacuation controlling valve 365 according to an embodiment of the present disclosure. In the embodiment of FIG. 4A, when the evacuation controlling valve 365 is slidingly drawn from the exhaust valve module 360, the through-hole 366 of the evacuation controlling valve 365 will align with the second opening 362 of the exhaust valve module 360. As such, the alignment will allow the second opening 362 of the exhaust valve module 360 to communicate with the first opening 361 and the third opening 363. FIG. 4B is a schematic diagram illustrating the closing of the evacuation controlling valve 365 according to an embodiment of the present disclosure. In the embodiment of FIG. 4B, when the evacuation controlling valve 365 is slidingly pushed into the exhaust valve module 360, the through-hole 366 of the evacuation controlling valve 365 staggers with the second opening 362 of the exhaust valve module 360. When the second opening 362 of the exhaust valve module 360 is blocked by the evacuation controlling valve 365, it cannot communicate with the first opening 361 and the third opening 363. It should be noted that the present disclosure is not limited thereto. In other embodiments, the evacuation controlling valve 365 may also be replaced with an element such as a movable valve.

Figure 5A:
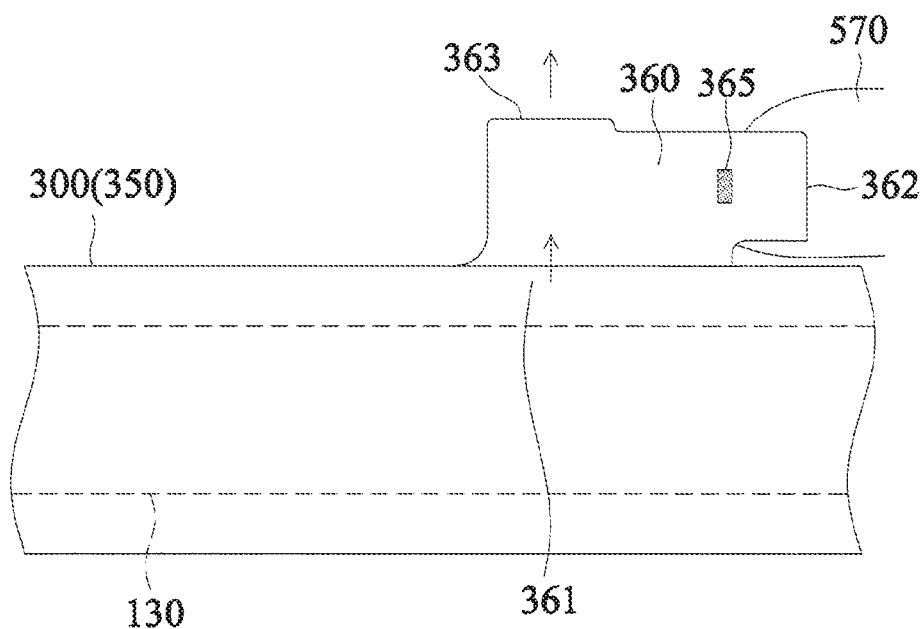
FIG. 5A is a schematic diagram of an exhaust device operating in a normal exhausting mode according to an embodiment of the present disclosure.
Figure 5B:
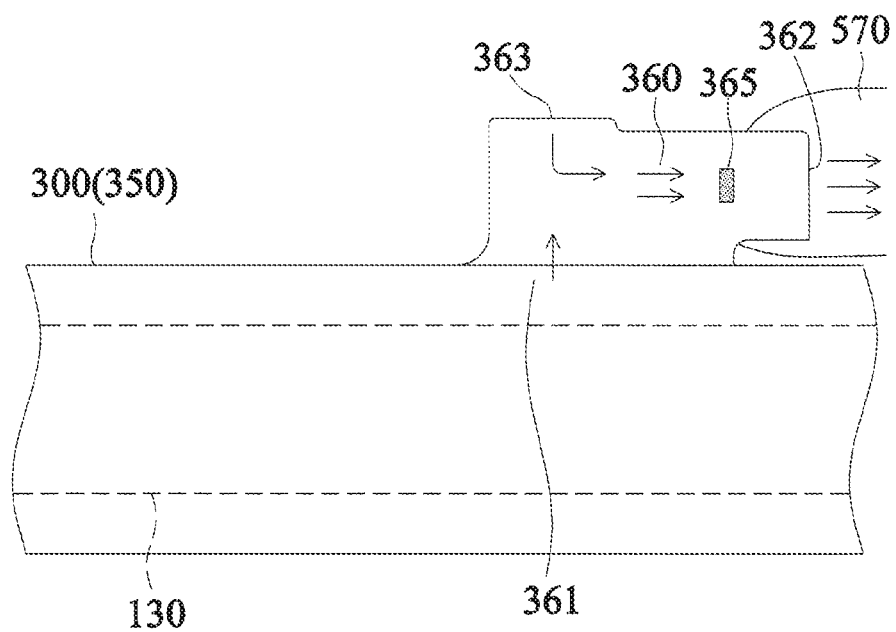
FIG. 5B is a schematic diagram of an exhaust device operating in a weak exhausting mode according to an embodiment of the present disclosure.
Figure 5C:
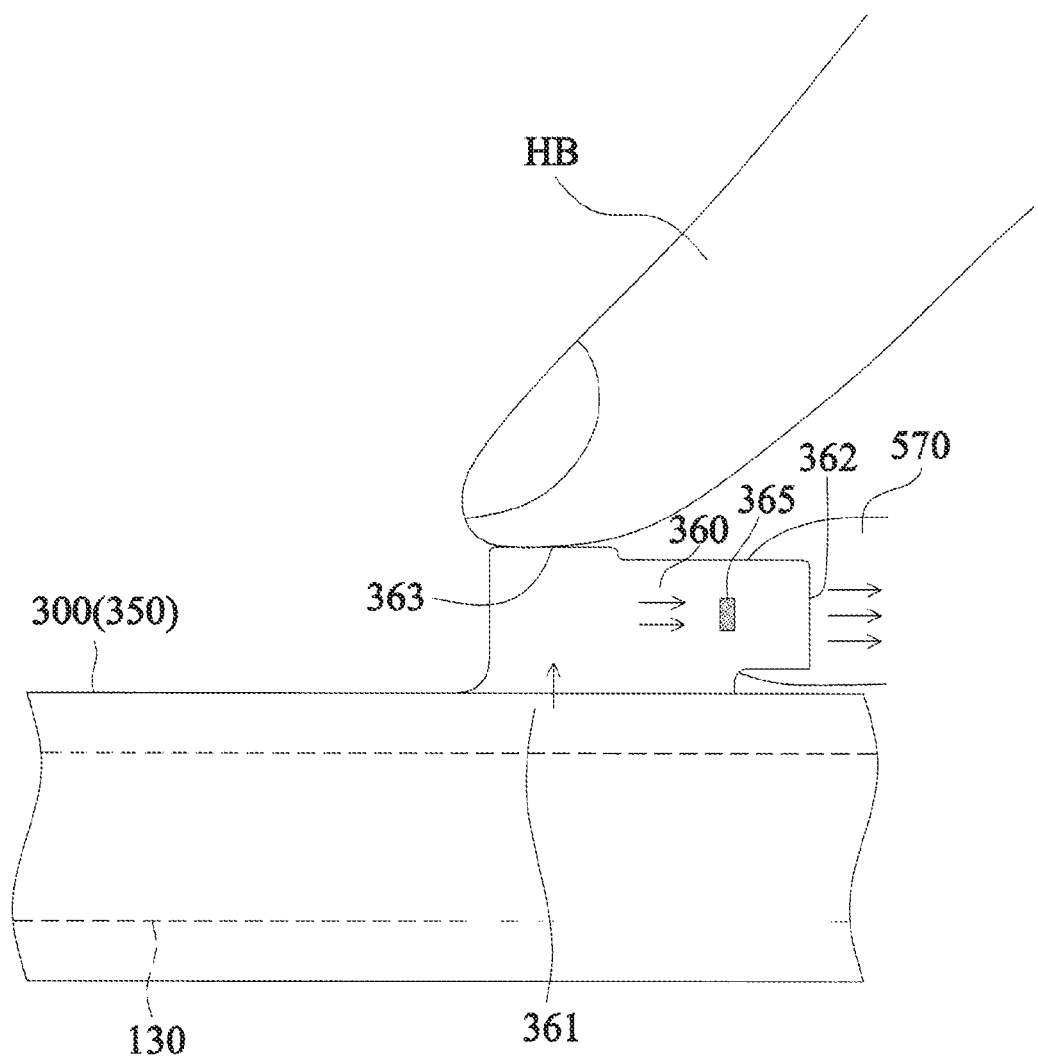
FIG. 5C is a schematic diagram of an exhaust device operating in a strong exhausting mode according to an embodiment of the present disclosure.

Referring to FIGS. 5A, 5B, and 5C, in some embodiments, the exhaust device 300 further includes a low-pressure evacuation device 570, wherein the low-pressure evacuation device 570 is connected to the second opening 362 of the T-shaped flow channel of the exhaust valve module 360, and evacuation can be performed via the second opening 362 of the T-shaped flow channel of the exhaust valve module 360. The low-pressure evacuation device 570 is used to accelerate the evacuation or removal of surgical waste. The aforementioned evacuation controlling valve 365 may be used to selectively enable or disable the low-pressure evacuation device 570. For example, when the evacuation controlling valve 365 allows communication between the first opening 361 and the second opening 362 of the T-shaped flow channel of the exhaust valve module 360, the low-pressure evacuation device 570 can be used to perform evacuation from the hollow interior of the tubular structure 350. This can be regarded as the low-pressure evacuation device 570 being enabled; on the contrary, when the evacuation controlling valve 365 blocks communication between the first opening 361 and the second opening 362 of the exhaust valve module 360, the low-pressure evacuation device 570 fails to withdraw substances from the hollow interior of the tubular structure 350. This can be considered as the low-pressure evacuation device 570 being disabled. By using the evacuation controlling valve 365 and the low-pressure evacuation device 570, the exhaust device 300 may operate in at least three different modes, which will be detailed in the following embodiments.

FIG. 5A is a schematic diagram illustrating the operation of the exhaust device 300 in a normal exhausting mode according to an embodiment of the present disclosure. In the embodiment of FIG. 5A, the evacuation controlling valve 365 disables the low-pressure evacuation device 570, and the third opening 363 of the T-shaped flow channel of the exhaust valve module 360 remains open, so that the exhaust device 300 operates in the normal exhausting mode. Since the abdominal cavity is typically under positive pressure (e.g., a pressure of higher than about 15 to 20 mmHg above atmospheric pressure) during the laparoscopic surgery, even if the low-pressure evacuation device 570 is not used, the substance generated in the process of the surgery (e.g., smoke) will enter the tubular structure 350 via the vents 355 due to the pressure difference, and is then automatically discharged via the third opening 363 of the T-shaped flow channel of the exhaust valve module 360. In other embodiments, when the exhaust device 300 is operated in the normal exhausting mode, the low-pressure evacuation device 570 may also be removed. At this time, the evacuation controlling valve 365 may be open or closed. In the normal exhausting mode, the positive pressure environment in the abdominal cavity can be maintained to prevent excessive gas leakage that leads to pressure loss, and save power consumption.

FIG. 5B is a schematic diagram illustrating the operation of the exhaust device 300 in a weak exhausting mode according to an embodiment of the present disclosure. In the embodiment of FIG. 5B, the evacuation controlling valve 365 enables the low-pressure evacuation device 570, and the third opening 363 of the T-shaped flow channel of the exhaust valve module 360 remains open, so that the exhaust device 300 is operated in a weak exhausting mode. At this time, in addition to the surgical waste entering the exhaust valve module 360 from the first opening 361, the gas entering the third opening 363 is also evacuated via the second opening 362 by the low-pressure evacuation device 570. Thus, the exhaust device 300 can provide a relatively weaker force for removing surgical waste.

FIG. 5C is a schematic diagram of the exhaust device 300 operating in a strong exhausting mode according to an embodiment of the present disclosure. In the embodiment of FIG. 5C, the evacuation controlling valve 365 enables the low-pressure evacuation device 570, and the third opening 363 of the T-shaped flow channel of the exhaust valve module 360 is closed (e.g., the third opening 363 can be pressed with a finger HB, or the third opening 363 is completely enclosed by other components). Therefore, the exhaust device 300 is operated in a strong exhausting mode. At this time, only the surgical waste entering the exhaust valve module 360 via the first opening 361 is evacuated via the second opening 362 by the low-pressure evacuation device 570, so that the exhaust device 300 can provide a relatively stronger force for removing surgical waste. The exhaust efficiency of the above three modes are listed from the order of high to low: strong exhausting mode, weak exhausting mode, and normal exhausting mode, but the normal exhausting mode can be performed without power consumption.

In some embodiments, the exhaust device 300 can also be used as a suction irrigation tube. For example, the low-pressure evacuation device 570 is disabled by the evacuation controlling valve 365, and a sterile saline solution is injected into the exhaust device 300 via the third opening 363 from an external syringe or an in-drip element. The saline solution is used to flush cells or organ tissues via the vents 355 along the tubular structure 350. Further, the low-pressure evacuation device 570 may be enabled by the evacuation controlling valve 365. In addition to removing smoke, the low-pressure evacuation device 570 may also extract blood or tissue residues from the abdominal cavity. In other embodiments, the strength of extraction can be adjusted through the opening or closing of the third opening 363.

In addition, the scalpel device 110 may be partially or completely retracted so that the blade portion 120 is retracted from the first end 351 of the tubular structure 350 into the tubular structure 350, whereby the first end 351 of the tubular structure 350 and the vents 355 can be used as a suction tube to enhance the effect. When the ancillary system is operated in this manner, it can be immediately used without the need to withdraw the scalpel device 110 or replace the scalpel device 110 with other instruments. Therefore, the surgical efficiency can be effectively improved.

In terms of the element size, the maximum outer diameter of the tubular structure 350 of the exhaust device 300 may be about 3 mm or more (e.g., 3.5 mm, 4 mm, 5 mm, 5.5 mm, 6 mm, 6.5 mm, 7 mm, 7.2 mm, 7.5 mm, 7.8 mm, 8 mm, 8.5 mm, 9 mm, 9.5 mm, 10 mm, 10.5 mm or 11 mm) for applying to a trocar having a minimum inner diameter of 8 mm, 10 mm, 12 mm, 15 mm or more. The length of the exhaust device 300 may be 20 cm, 25 cm, 27 cm, 29 cm, 32 cm, 36 cm, 40 cm, 42 cm or 45 cm depending on the length of the scalpel device 110 and clinical needs. In this type of design, the exhaust device 300 can be attached to any scalpel device, such as the da Vinci surgical instrument.

The exhaust device 300 of the present disclosure can provide an exhaust channel for a large amount of smoke generated upon turning on the scalpel device 110 (e.g., an electrical scalpel, a bipolar scalpel, Ligasure, a harmonic scalpel, laser, etc.). In the present disclosure, the distances between the blade portion 120 of the scalpel device 110 and the vents 355 of the exhaust device 300 are close (e.g., the distances between the tip 122 of the blade portion 120 and the vents 355 can be only between 1 cm and 2 cm). When smoke is generated from the tip 122 of the blade portion 120, it can be removed immediately before diffusing to the entire abdominal cavity. For example, the effect of smoke evacuation is more significantly improved in a stenotic surgical environment (e.g., pelvic cavity), specific site surgery (e.g., endoscopic prostatic surgery, transanal endoscopic surgery, head-and-neck surgery, gynecological surgery, urological surgery), thoracic surgery, laparoscopic single-site surgery or other surgeries that may produce smoke plumes in body cavities.

According to one embodiment of the present disclosure, the exhaust device 300 is not integrally formed with the scalpel device 110, and both of the exhaust device 300 and the scalpel device 110 are eligible to disassemble. Therefore, the exhaust device 300 can be used alone, and is disposable, thereby saving the overall treatment cost of the surgery, since the scalpel device 110 is generally more expensive and it is often reused after sterilization.

Furthermore, the exhaust device 300 of the present disclosure may be manufactured according to general specifications, so that it can be directly applied to various brands of scalpel devices (e.g., applicable to all laparoscopic scalpels such as 5 mm scalpels, but not limited thereto), thereby having commercial value for mass production.

In addition, the exhaust device 300 of the present disclosure may also be used as a suction irrigation tube to avoid frequent replacement of the device program and improve the surgical efficiency.

It is noteworthy that the above sizes, shapes, and parameters of elements are not limitations of the present disclosure. Device designers can adjust these settings based on medical needs. The ancillary system and the exhaust device for surgery of the present disclosure are not limited to the states illustrated in the drawings of the present disclosure. The present disclosure may include only any one or more of the features of any one or more of the embodiments shown in the drawings. In other words, not all illustrated features must be simultaneously implemented in the ancillary system and the exhaust device for surgery of the present disclosure.

The numbers in this specification and the claims, such as "first," "second," "third," etc. have no sequential relationship with each other, and are used for merely distinguishing between two different elements with the same name.

Although the present disclosure has been disclosed in the above embodiments, they are not intended to limit the scope of the present disclosure. Any one skilled in the art can make a few changes and embellishment without departing from the spirit and scope of the present disclosure. Therefore, the scope of the present disclosure shall be accorded to the definitions set forth in the appended claims.

What is claimed is:

1. An ancillary system for surgery, comprising:
an exhaust device comprising a tubular structure with a first end and a second end departed from the first end, and a head portion disposed at the first end, wherein a surface of the head portion has one or more vents formed thereon; and
an exhaust valve module connected to the tubular structure and configured for a substance generated during a surgical procedure to enter the tubular structure via the one or more vents and be discharged through the exhaust valve module, wherein the exhaust valve module comprises:
an exhaustion-adjustable flow channel, and the exhaustion-adjustable flow channel has a first opening directly disposed on the tubular structure of the exhaust device, a second opening configured for connecting to an evacuation device, and a third opening in communication with the first opening and the second opening, and
an evacuation controlling valve disposed between the first opening and the second opening and configured to selectively open or close the second opening of the exhaustion-adjustable flow channel to enable or disable the evacuation device,
wherein the evacuation device is disabled by the evacuation controlling valve and the third opening of the exhaustion-adjustable flow channel of the exhaust valve module remains open, such that the exhaust device is configured to operate in a normal exhausting mode, wherein the evacuation device is enabled by the evacuation controlling valve and the third opening of the exhaustion-adjustable flow channel of the exhaust valve module is closed, such that the exhaust device is configured to operate in a strong exhausting mode to provide a first suction force, wherein the evacuation device is enabled by the evacuation controlling valve and the third opening of the exhaustion-adjustable flow channel of the exhaust valve module remains open, such that the exhaust device is configured to operate in a weak exhausting mode to provide a second suction force, and the first suction force is greater than the second suction force.

2. The ancillary system of claim 1, further comprising a trocar, wherein the exhaust device is disposed in the trocar.

3. The ancillary system of claim 1, further comprising a scalpel device, and the scalpel device comprises a blade portion and a connecting arm connected to the blade portion.

4. The ancillary system of claim 3, wherein the connecting arm of the scalpel device is at least partially disposed inside the tubular structure of the exhaust device.

5. The ancillary system of claim 3, wherein the first end of the tubular structure is adjacent to or aligned with a bottom of the blade portion of the scalpel device.

6. The ancillary system of claim 3, wherein the blade portion of the scalpel device is at least partially retractable from the first end of the tubular structure.

7. The ancillary system of claim 3, wherein the exhaust device is coupled to the scalpel device in a detachable manner.

8. The ancillary system of claim 1, wherein the head portion has a cone-shape structure.

9. The ancillary system of claim 8, wherein the cone-shape structure has a longitudinal axis being different than a longitudinal axis of the tubular structure.

10. The ancillary system of claim 1, wherein the tubular structure is made of a transparent material.

11. The ancillary system of claim 1, wherein the head portion is made of a transparent material.

12. The ancillary system of claim 1, wherein the exhaust valve module is adjacent to the second end of the tubular structure.

13. The ancillary system of claim 1, wherein the exhaustion-adjustable flow channel is a T-shaped flow channel.

* * * * *